United States Patent [19]

Haskell

[11] Patent Number: 5,550,296
[45] Date of Patent: Aug. 27, 1996

[54] METHOD OF PRODUCING KETONES

[75] Inventor: Weston W. Haskell, Fulshear, Tex.

[73] Assignee: Shell Oil Company, Houston, Tex.

[21] Appl. No.: 348,642

[22] Filed: Dec. 2, 1994

[51] Int. Cl.$^6$ .................................................. C07C 45/45
[52] U.S. Cl. ........................ 568/314; 562/490; 562/511
[58] Field of Search ................................. 562/511, 490; 568/314

[56] References Cited

U.S. PATENT DOCUMENTS

| | | | |
|---|---|---|---|
| 2,186,249 | 1/1940 | Lazar et al. | 562/511 |
| 2,815,372 | 12/1957 | Portser | 562/511 |
| 3,176,041 | 3/1965 | Ayers et al. | 562/511 |
| 3,341,603 | 9/1967 | Leaman | 562/511 |
| 5,011,579 | 4/1991 | Davis | 562/490 |

Primary Examiner—James H. Reamer
Attorney, Agent, or Firm—Kim Muller

[57] ABSTRACT

A liquid ammonia stream is mixed with a crude oil stream which contains naphthenic acids. Ammonium naphthenates are formed which are then separated from the crude oil with the ammonia. The naphthanates are converted back to acids by addition of acetic acid. Calcium hydroxide is added to form calcium naphthenates and the mixture is pyrolysized which produces ketones.

14 Claims, 1 Drawing Sheet

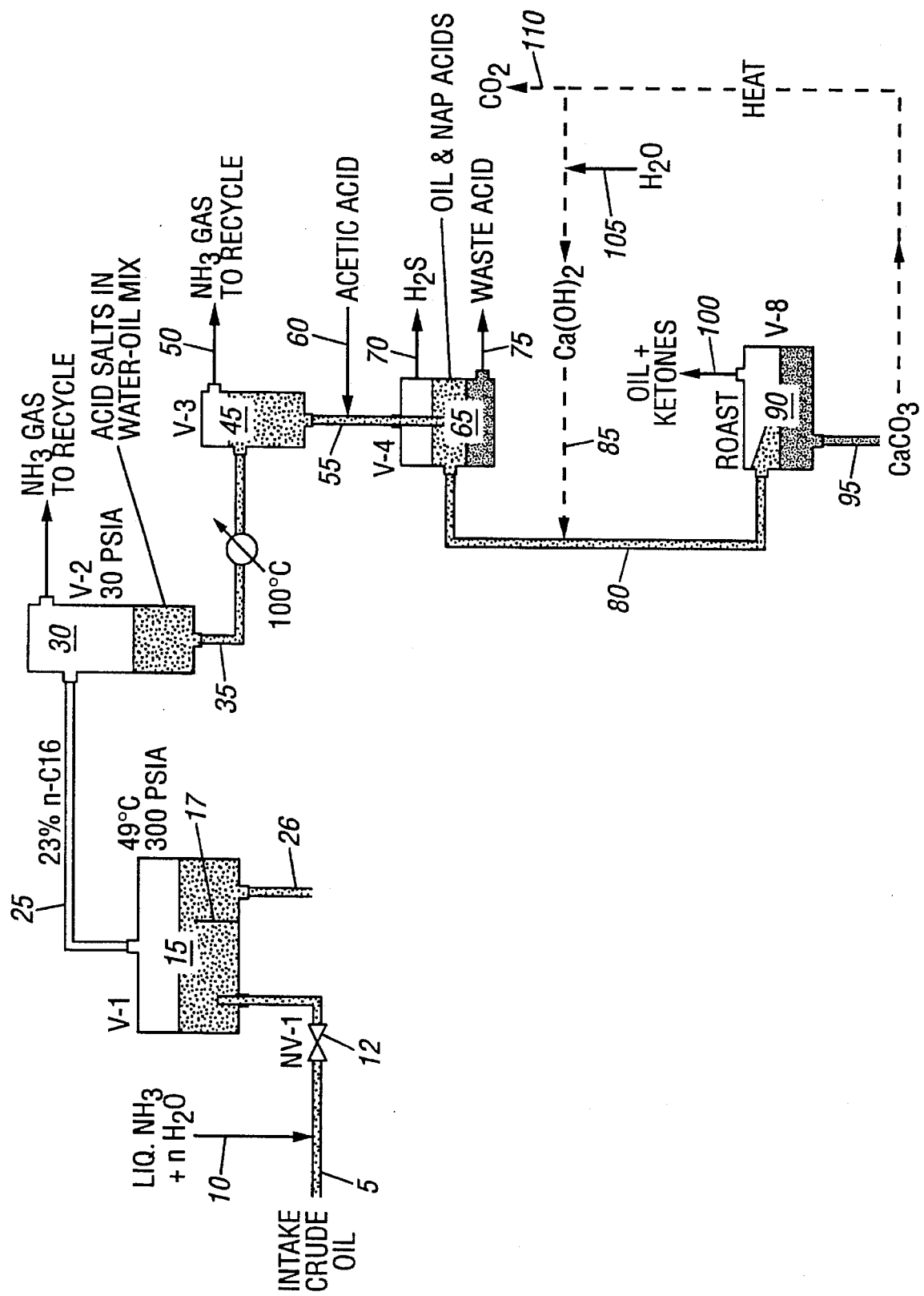

METHOD OF PRODUCING KETONES

FIELD OF THE INVENTION

The invention relates to a method of producing ketones. More particularly the invention relates to a method of producing ketones from naphthenic acids in crude oils.

BACKGROUND OF THE INVENTION

Many crude oils have a high naphthenic acid content. This reduces the value of the crude oil since the acid content can cause corrosion in the processing equipment. Expensive corrosion resistant equipment must be used or non-corrosion resistant equipment must be frequently maintained or replaced. Once the acid is removed it creates an disposal problem. There are increasing environmental concerns relating to disposing of chemical wastes as well as increasing costs for disposing of hazardous materials. It would be advantageous to have a process for making a useful product from the naphthenic acids in high density crude oils thus avoiding the need of disposing of environmentally hazardous materials.

SUMMARY OF THE INVENTION

The present invention includes a process for producing ketones from naphthenic acids found in many crude oils. A liquid ammonia stream is mixed with a crude oil stream which contains naphthenic acids. Ammonium naphthenates are formed which are then separated from the crude oil with the ammonia. The naphthenates are converted back to acids by addition of acetic acid. Calcium hydroxide is added and then the mixture is pyrolysized which produces naphthenic ketones. Thus the need is avoided for disposal of environmentally hazardous materials.

BRIEF DESCRIPTION OF THE DRAWINGS

The FIGURE depicts the process flow paths for an aspect of this invention of reducing waste disposal by converting naphthenic acids from crude oil into ketones.

DETAILED DESCRIPTION OF THE INVENTION

An aspect of the instant invention is a process for producing ketones from the naphthenic acids found in many crude oils. With reference to the figure liquid ammonia stream 10 is injected into the crude oil feed 5. An amount of liquid ammonia effective to convert substantially all the naphthenic acids to ammonium napthenates is injected. Optionally, additional liquid ammonia is added to react with any hydrogen sulfide or mercaptans present in the crude oil. Preferably from about 0.1% wt. to about 8% wt., more preferably from about 1% wt to about 6% wt., liquid ammonia based on the crude oil is injected. To obtain substantial mixing this injection is upstream of a mixing valve 12. The resulting mixture is fed to a first separation vessel 15.

Naphthenic acids in the crude oil will be converted to ammonium naphthenates by the following reaction (1):

$$RCOOH + NH_3 \rightarrow RCOO^- + NH_4^+ \quad (1)$$

If hydrogen sulfide is in the crude oil it will react with ammonia to produce ammonium bisulfide by the following reaction (2):

$$H_2S + NH_3 \rightarrow NH_4^+ + HS^- \quad (2)$$

As ammonia is a strong base any mercaptans will react similarly to hydrogen sulfide by the following reaction (3):

$$RSH + NH_3 \rightarrow NH_4^+ RS^- \quad (3)$$

In first separation vessel 15 the liquid ammonia is less dense than the crude oil and will float to the top. For example, at 49° C. liquid ammonia will have a density of 0.56 g/cc. Any typical crude oil containing naphthenic acids is suitable for use in the process of this invention since it will have a higher density than that of liquid ammonia. The ammonium naphthenates, and optionally any ammonium bisulfide or hydrogen sulfide present, will transfer preferentially to the liquid ammonia phase. The crude oil/ammonia separation is optionally accelerated by an electric field between grids 17 in the bottom of first separation vessel 15. The temperature of the mixture in first separation vessel 15 is below the critical temperature of liquid ammonia. Preferably the temperature is from about 35° C. to about 70° C., more preferably the temperature is from about 45° C. to abut 55° C. The mixture is at a pressure effective to prevent the liquid ammonia from becoming gaseous ammonia. Preferably, the pressure is from about 200 psia to about 200 psia, more preferably the pressure is from about 275 psia to about 325 psia.

Water is usually present in the crude oil feed 5. The water will dilute the liquid ammonia and will separate to the liquid ammonia phase. Naphthenates are more soluble in water than in liquid ammonia. Therefore, depending on the water content of the crude oil, water is added to liquid ammonia stream 10 in an amount effective to preferentially dissolve substantially all the naphthenates in the liquid ammonia phase. Preferably, not more than about 10% wt. water based on the liquid ammonia is added to liquid ammonia stream 10. Addition of water to the liquid ammonia stream to increase solubility of the naphthenates in the ammonia phase is controlled so that the ammonia phase density remains significantly less than the crude oil density.

Hydrocarbons in the crude oil are slightly soluble in the liquid ammonia and will therefore there will be some carryover into the liquid ammonia phase. This is optionally controlled by the addition of water to liquid ammonia stream 10. Adding water will reduce hydrocarbon solubility, while at the same time increasing naphthenate solubility in the ammonia phase. The concentration of hydrocarbons in the ammonia phase is from about 1.5% wt to about 3% wt., or preferably about 1.75% wt. to about 2.5% wt., based on the ammonia phase total weight.

Once the crude oil and liquid ammonia phases are separated the crude oil phase is removed through line 26. The liquid ammonia phase is removed by line 25 and is passed to second separation vessel 30. In second separation vessel 30 the liquid ammonia is flashed off leaving an aqueous phase containing the ammonium naphthenates and a water-oil emulsion. The hydrocarbons cannot be separated at this point because the water-oil emulsion will be stabilized by the naphthenates. These hydrocarbons can be recovered during the later step of pyrolysizing the calcium salts as discussed below.

The aqueous phase in second separation vessel 30 is heated as it is passed through line 35 to third separation vessel 45. It is heated to an effective temperature such that any remaining ammonia is removed as a gas through line 50. Preferably, it is heated above about 75° C., more preferably from about 90° C. to about 125° C. The remaining liquid contains the remaining hydrocarbons, naphthenates, and some sulfides.

This liquid is then passed through line 55 where it is admixed with an amount of dilute acetic acid, fed through line 60, effective to convert substantially all the naphthenates to naphthenic acids. Any mercaptans and hydrogen sulfide are separated from the aqueous phase. Three phases, i.e., naphthenic acids, hydrocarbon, and aqueous, are separated in fourth separation vessel 65. Hydrogen sulfide will be removed as a gas through line 70. The bottom liquid phase is the dilute acid which is removed through line 75. The upper liquid phase is the naphthenic acids.

The naphthenic acids and hydrocarbon phases are passed from fourth separation vessel 65 through line 80. Slaked lime, $Ca(OH)_2$, is fed through line 85 and mixed with the naphthenic acids. This will convert the naphthenic acids to calcium salts. This mixture is then passed to pyrolysis unit 90. The calcium salts of naphthenic acids are heated to a temperature effective to produce naphthenic ketones and calcium carbonate as in equation (4):

$$Ca^{++}(RCOO^-)_2 \rightarrow CaCO_3 + RCOR \qquad (4)$$

Preferably the calcium salts are heated to a temperature of from about 700° C. to about 90° C., more preferably from about 750° C. to about 850° C.

The resulting ketones and any dissolved hydrocarbons are removed as a vapor through line 100. Thus the naphthenic acids are converted to products which are mixtures of higher ketones. These could be fractionated into gasoline boiling range products. Acetone may be recoverable from the lighter boiling range products.

Calcium carbonate is passed through line 95. Heating the calcium carbonate will produce lime (CaO) and $CO_2$. The $CO_2$ is recovered in line 110. The lime is hydrated through line 105 which produces calcium hydroxide. The conditions for production of calcium hydroxide from calcium carbonate are conventional. The calcium hydroxide is then recycled through line 85.

The invention is further described in the following illustrative embodiment. The illustrative embodiment are for illustrative purposes only and are not intended to limit the scope of the invention in any way.

ILLUSTRATIVE EMBODIMENT

A heavy crude oil feed containing naphthenic acids is admixed with about 8% wt. liquid ammonia stream based on the crude oil feed where the liquid ammonia stream contains about 10% wt. water based on the liquid ammonia. The mixture passes through a mixing valve and the naphthenic acids react with the ammonia to form ammonium naphthenates. The mixture passes to a separation vessel. The oil and liquid ammonia are separated by density deferential and with the aid of an electric grid in the bottom of the vessel to form oil and ammonia phases.

The naphthenates dissolve in the ammonia phase. The ammonia phase is removed to a second separation vessel where ammonia is flashed off. The remaining mixture is water, dissolved hydrocarbons, and naphthenates. This mixture is heated and sent to a third separation vessel where any remaining ammonia is removed. Acetic acid is added to the remaining mixture which converts the naphthenates to naphthenic acids. In a fourth vessel any excess acetic acid is recovered and any hydrogen sulfide is removed. The naphthenic acid and any hydrocarbons are then mixed with calcium hydroxide to form calcium salts. These calcium salts are then pyrolysized producing ketones which are recovered as a gas. Accordingly, substantially all the naphthenic acids in the original crude oil feed are converted to ketones.

What is claimed is:

1. A method of producing ketones from crude oil containing naphthenic acids thereby reducing waste disposal of naphthenic acids comprising:
    (a) admixing a liquid ammonia stream comprising water and liquid ammonia with a crude oil stream comprising hydrocarbons and naphthenic acids to obtain a mixture comprising liquid ammonia, ammonium naphthenates, water, and oil;
    (b) separating the mixture into a liquid ammonia phase comprising liquid ammonia, water and substantially all the naphthenates and an oil phase;
    (c) feeding said liquid ammonia phase to a first separation vessel;
    (d) separating at least a portion of said liquid ammonia as gaseous ammonia from said liquid ammonia phase to obtain a first mixture comprising naphthenates and water;
    (e) acidifying said first mixture with acetic acid to convert said naphthenates to naphthenic acids and to obtain a second mixture comprising naphthenic acids and water;
    (f) recovering excess acetic acid;
    (g) admixing calcium hydroxide with said second mixture to produce calcium salts of naphthenic acids; and
    (h) pyrolysizing said calcium salts to produce naphthenic ketones.

2. The method of claim 1 wherein in step (c) said liquid ammonia phase further comprises from about 1.5% wt to about 3% wt. oil.

3. The method of claim 2 wherein said separation in step (d) is performed at a pressure of from about 400 psia to about 200 psia and at a temperature of from about 35° C. to about 70° C.

4. The method of claim 1 wherein said pyrolysis in step (h) is performed at a temperature of from about 700° C. to about 900° C.

5. The method of claim 2 wherein said first mixture contains residual ammonia and wherein the first mixture is heated to remove said residual ammonia.

6. The method of claim 1 wherein said pyrolysizing in step (h) further produces calcium carbonate.

7. The method of claim 6 wherein said calcium carbonate is heated to produce quick lime and carbon dioxide, wherein said carbon dioxide is separated off and wherein water is added to said quick lime to produce calcium hydroxide and wherein said calcium hydroxide is recycled to step (g).

8. A method of treating a crude oil stream to reduce problems of waste disposal of naphthenic acids by conversion of said acids to ketones comprising:
    (a) admixing a liquid ammonia stream comprising water and liquid ammonia with said crude oil stream comprising hydrocarbons and naphthenic acids to obtain a mixture of from 1.5% wt. to about 3% wt. oil, and liquid ammonia and ammonium naphthenates;
    (b) separating the mixture at a pressure of from about 200 psia to about 400 psia and at a temperature of from about 35° C. to about 70° C. into a liquid ammonia phase comprising liquid ammonia, water and substantially all the naphthenates and an oil phase;
    (c) feeding said liquid ammonia phase to a first separation vessel;
    (d) separating said liquid ammonia as gaseous ammonia from said liquid ammonia phase to obtain a first mixture comprising naphthenates and water;

(e) admixing said first mixture with acetic acid to convert said naphthenates to naphthenic acids and to obtain a second mixture comprising naphthenic acids and water;

(f) recovering excess acetic acid;

(g) admixing calcium hydroxide with said second mixture to produce calcium salts of naphthenic acids; and (h) pyrolysizing said calcium salts at a temperature of from about 700° C. to about 900° C. to produce naphthenic ketones.

9. The method of claim 8 wherein in step (c) said liquid ammonia phase further comprises from about 1.75% wt to about 2.5% wt. oil.

10. The method of claim 8 wherein said separation in step (d) is performed at a pressure of from about 275 psia to about 325 psia and at a temperature of from about 45° C. to about 55° C.

11. The method of claim 10 wherein said pyrolysis in step (h) is performed at a temperature of from about 750° C. to about 850° C.

12. The method of claim 8 wherein said first mixture which contains residual ammonia is heated to remove said residual ammonia.

13. The method of claim 12 wherein said pyrolysizing in step (h) produces calcium carbonate.

14. The method of claim 13 wherein said calcium carbonate is heated to produce quick lime and carbon dioxide, wherein said carbon dioxide is separated off and wherein water is added to said quick lime to produce calcium hydroxide and wherein said calcium hydroxide is recycled to step (g).

* * * * *